US012734730B2

(12) United States Patent
Shastry et al.

(10) Patent No.: US 12,734,730 B2
(45) Date of Patent: Sep. 15, 2026

(54) HYBRID METHOD OF FORMING MICROSTRUCTURE ARRAY MOLDS, METHODS OF MAKING MICROSTRUCTURE ARRAYS, AND METHODS OF USE

(71) Applicant: Panther Life Sciences Corporation, Normandy Park, WA (US)

(72) Inventors: Ashutosh Shastry, Santa Clara, CA (US); Wesley Chang, Fremont, CA (US); Parminder Singh, Union City, CA (US)

(73) Assignee: Panther Life Sciences Corporation, Normandy Park, WA (US)

( * ) Notice: Subject to any disclaimer, the term of this patent is extended or adjusted under 35 U.S.C. 154(b) by 0 days.

(21) Appl. No.: 18/660,496

(22) Filed: May 10, 2024

(65) Prior Publication Data

US 2025/0114981 A1 Apr. 10, 2025

Related U.S. Application Data

(63) Continuation of application No. 17/255,420, filed as application No. PCT/US2019/039028 on Jun. 25, 2019, now abandoned.

(Continued)

(51) Int. Cl.

*B29C 33/38* (2006.01)
*A61M 37/00* (2006.01)

(Continued)

(52) U.S. Cl.

CPC ..... *B29C 33/3857* (2013.01); *A61M 37/0015* (2013.01); *G03F 7/0002* (2013.01);

(Continued)

(58) Field of Classification Search

CPC ........... B29C 33/3857; A61M 37/0015; A61M 2037/0053; G03F 7/0002; G03F 7/0015;

(Continued)

(56) References Cited

U.S. PATENT DOCUMENTS

| | | | |
|---|---|---|---|
| 3,964,482 | A | 6/1976 | Gerstel et al. |
| 6,219,574 | B1 | 4/2001 | Cormier et al. |

(Continued)

FOREIGN PATENT DOCUMENTS

| | | | |
|---|---|---|---|
| CN | 1623515 | A | 6/2005 |
| CN | 102026910 | A | 4/2011 |

(Continued)

OTHER PUBLICATIONS

JP Application No. 2020-571757, Office Action dated Jan. 30, 2023; Applicant Corium Pharma Solutions, Inc.; 9 pages with English translation.

(Continued)

*Primary Examiner* — Jamel M Nelson
*Assistant Examiner* — Erica Hartsell Funk

(57) ABSTRACT

A method of forming a master mold (52), comprising: a) forming a plurality of microstructure portions (42) in a substrate formed of a first material by a first micromachining process, each microstructure portion comprising a shaft (40) and a distal tip (38); b) preparing a negative mold (46) of the plurality of microstructure portions, wherein the mold is formed of a second material and comprises a plurality of cavities (48) corresponding to each microstructure portion in the plurality of microstructure portions (42); c) electroplating a metal (50) onto the negative mold to fill each cavity in the plurality of cavities and to form a base layer (54) extending from the negative mold; d) forming a proximal section (56) for each of the microstructures in the base layer using a second micromachining process (e.g. mechanical (Continued)

micromachining); and e) before or after said step d), removing the negative mold from the metal to form a master mold.

26 Claims, 5 Drawing Sheets

Related U.S. Application Data

(60) Provisional application No. 62/689,640, filed on Jun. 25, 2018.

(51) Int. Cl.

| | |
|---|---|
| ***G03F 7/00*** | (2006.01) |
| ***G03F 7/038*** | (2006.01) |
| ***G03F 7/039*** | (2006.01) |
| ***G03F 7/075*** | (2006.01) |
| ***G03F 7/20*** | (2006.01) |
| *B29L 31/00* | (2006.01) |

(52) U.S. Cl.
CPC .......... *G03F 7/0015* (2013.01); *G03F 7/0382* (2013.01); *G03F 7/0392* (2013.01); *G03F 7/0755* (2013.01); *G03F 7/2016* (2013.01); *A61M 2037/0053* (2013.01); *B29L 2031/757* (2013.01)

(58) Field of Classification Search
CPC .... G03F 7/0382; G03F 7/0392; G03F 7/0755; G03F 7/2016; B29L 2031/757
See application file for complete search history.

(56) References Cited

U.S. PATENT DOCUMENTS

| | | | |
|---|---|---|---|
| 6,451,240 | B1 | 9/2002 | Sherman et al. |
| 6,652,478 | B1 | 11/2003 | Gartstein et al. |
| 6,849,558 | B2 | 2/2005 | Schaper |
| 6,945,952 | B2 | 9/2005 | Kwon |
| 7,763,203 | B2 | 7/2010 | Arias et al. |
| 7,785,301 | B2 | 8/2010 | Yuzhakov |
| 8,603,384 | B2 | 12/2013 | Lüttge et al. |
| 9,597,822 | B2 | 3/2017 | Mitamura |
| 11,179,553 | B2 | 11/2021 | Kendall et al. |
| 2002/0082543 | A1 | 6/2002 | Park et al. |
| 2003/0228759 | A1 | 12/2003 | Uehara et al. |
| 2004/0007796 | A1* | 1/2004 | Lastovich .............. B29C 33/42 264/222 |
| 2004/0087992 | A1 | 5/2004 | Gartstein et al. |
| 2005/0197308 | A1 | 9/2005 | Dalton et al. |
| 2008/0063866 | A1 | 3/2008 | Allen et al. |
| 2008/0269685 | A1 | 10/2008 | Singh et al. |
| 2010/0304064 | A1 | 12/2010 | Huttner |
| 2011/0006458 | A1 | 1/2011 | Sagi et al. |
| 2011/0192562 | A1 | 8/2011 | Motoi et al. |
| 2011/0276027 | A1 | 11/2011 | Trautman et al. |
| 2011/0276028 | A1 | 11/2011 | Singh et al. |
| 2013/0292868 | A1 | 11/2013 | Singh et al. |
| 2014/0180201 | A1 | 6/2014 | Ding et al. |
| 2014/0272101 | A1 | 9/2014 | Chen et al. |
| 2014/0276366 | A1 | 9/2014 | Bourne et al. |
| 2014/0276580 | A1 | 9/2014 | Le et al. |
| 2017/0095947 | A1 | 4/2017 | Ogawa et al. |
| 2017/0274196 | A1 | 9/2017 | Nordon et al. |
| 2018/0250851 | A1 | 9/2018 | Ogawa et al. |
| 2020/0197679 | A1 | 6/2020 | Li et al. |
| 2021/0276228 | A1 | 9/2021 | Shastry et al. |

FOREIGN PATENT DOCUMENTS

| | | | |
|---|---|---|---|
| CN | 102202723 | A | 9/2011 |
| CN | 104067171 | A | 9/2014 |
| CN | 105498082 | A | 4/2016 |
| CN | 107538652 | A | 1/2018 |
| EP | 1377338 | A2 | 1/2004 |
| EP | 2155418 | A1 | 2/2010 |
| JP | 2003071849 | A | 3/2003 |
| JP | 2007118422 | A | 5/2007 |
| JP | 2009061745 | A | 3/2009 |
| JP | 2009184117 | A | 8/2009 |
| JP | 2011083387 | A | 4/2011 |
| JP | 2016030072 | A | 3/2016 |
| JP | 2016510375 | A | 4/2016 |
| JP | 2017071094 | A | 4/2017 |
| KR | 20130005353 | A | 1/2013 |
| WO | WO-2002053193 | A2 | 7/2002 |
| WO | WO-2002072189 | A2 | 9/2002 |
| WO | WO-2010096072 | A1 | 8/2010 |
| WO | WO-2012054582 | A2 | 4/2012 |
| WO | WO-2012153266 | A2 | 11/2012 |
| WO | WO-2016033540 | A1 | 3/2016 |
| WO | WO-2016036866 | A1 | 3/2016 |
| WO | WO-2016149152 | A1 | 9/2016 |
| WO | WO-2017056895 | A1 | 4/2017 |
| WO | WO-2017116076 | A1 | 7/2017 |

OTHER PUBLICATIONS

JP Application No. 2020-571757, Office Action dated May 30, 2023; Applicant Corium Pharma Solutions, Inc.; 9 pages with English translation.

Park et al. "Biodegradable polymer microneedles: fabrication, mechanics and transdermal drug delivery." Journal of controlled release. May 5, 2005;104(1):51-66.

Park et al. "Polymer microneedles for controlled-release drug delivery." Pharmaceutical research. May 2006; 23:1008-1019.

Park et al. "Polymer particle-based micromolding to fabricate novel microstructures." Biomedical Microdevices. Apr. 2007;9:223-234.

PCT Application No. PCT/US2019/039028, International Preliminary Report on Patentability dated Dec. 29, 2020; Applicant Corium, Inc.; 11 pages.

PCT Application No. PCT/US2019/039028, International Search Report and Written Opinion dated Sep. 13, 2019; Applicant Corium, Inc.; 6 pages.

Pharmacosmos, "Dextran 1," [online] [retrieved on Feb. 10, 2025]. Retrieved from the Internet: URL: [https://dextran.com/product-categories/pharmaceutical-quality-dextran/dextran-1/], 6 pages.

Pharmacosmos, "Dextran 10," [online] [retrieved on Feb. 10, 2025]. Retrieved from the Internet: URL: [https://dextran.com/product-categories/pharmaceutical-quality-dextran/dextran-10]/, 4 pages.

Pharmacosmos, "Dextran 20," [online] [retrieved on Feb. 10, 2025]. Retrieved from the Internet: URL: [https://dextran.com/product-categories/pharmaceutical-quality-dextran/dextran-20/], 4 pages.

Pharmacosmos, "Dextran 40," [online] [retrieved on Feb. 10, 2025]. Retrieved from the Internet: URL: [https://dextran.com/product-categories/pharmaceutical-quality-dextran/dextran-40/], 8 pages.

Pharmacosmos, "Dextran 70," [online] [retrieved on Feb. 10, 2025]. Retrieved from the Internet: URL: [https://dextran.com/product-categories/pharmaceutical-quality-dextran/dextran-70/], 8 pages.

Pharmacosmos, "Dextran 75." [online] [retrieved on Feb. 10, 2025]. Retrieved from the Internet: [URL: https://go.drugbank.com/salts/DBSALT002685], 10 pages.

U.S. Appl. No. 17/255,420, Office Action dated Aug. 25, 2023; Inventor Shastry, Ashutosh et al.; 7 pages.

* cited by examiner 18
16
14
20
22
12
10

24
28
26

30
32
34
36
40
38
42

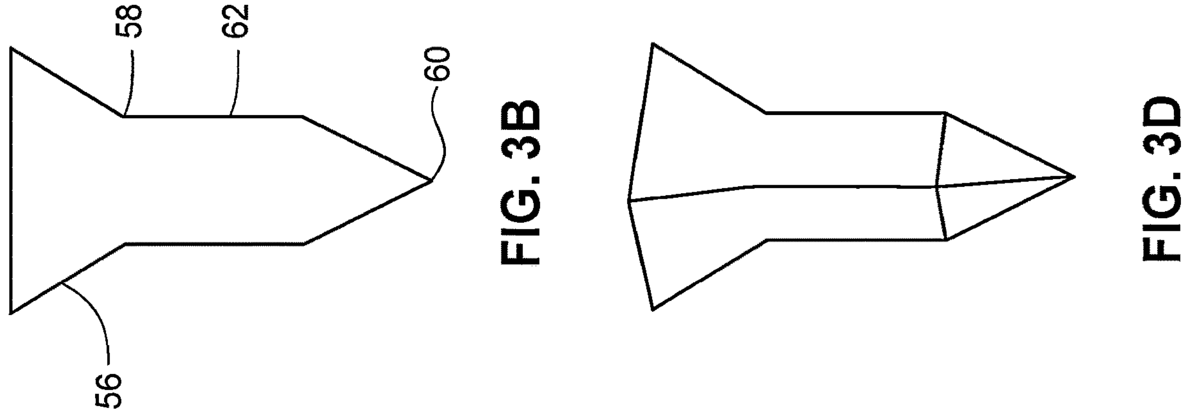
FIG. 3B
FIG. 3D
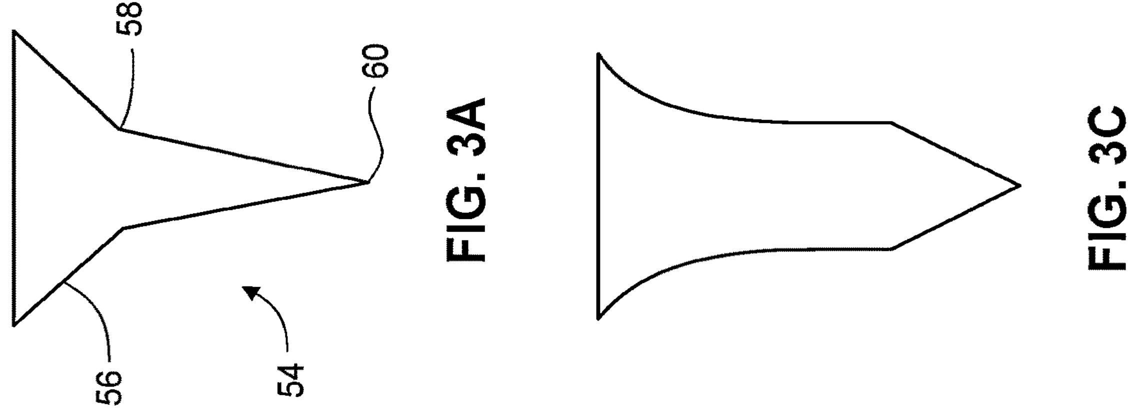
FIG. 3A
FIG. 3C

HYBRID METHOD OF FORMING MICROSTRUCTURE ARRAY MOLDS, METHODS OF MAKING MICROSTRUCTURE ARRAYS, AND METHODS OF USE

CROSS-REFERENCE TO RELATED APPLICATIONS

This application is a continuation of U.S. application Ser. No. 17/255,420, filed on Dec. 22, 2020, which is a U.S. national stage application under 37 U.S.C. § 371 which claims the benefit of priority to International Application No. PCT/US2019/039028, filed on Jun. 25, 2019, which claims the benefit of U.S. Provisional Application No. 62/689,640, filed on Jun. 25, 2018, incorporated herein by reference in its entirety.

TECHNICAL FIELD

The disclosure relates generally to methods for making or fabricating molds for making microstructure arrays, methods of using the molds for making microstructure arrays, and related features thereof.

BACKGROUND

Arrays of microneedles were proposed as a way of administering drugs through the skin in the 1970s, for example in expired U.S. Pat. No. 3,964,482. Microneedle, microprojection or microstructure arrays can facilitate the passage of drugs through or into human skin and other biological membranes in circumstances where ordinary transdermal administration is inadequate. Microstructure arrays can also be used to sample fluids found in the vicinity of a biological membrane such as interstitial fluid, which is then tested for the presence of biomarkers.

In recent years it has become more feasible to manufacture microstructure arrays in a way that makes their widespread use financially feasible. U.S. Pat. No. 6,451,240 discloses some methods of manufacturing microneedle arrays. If the arrays are sufficiently inexpensive, for example, they may be marketed as disposable devices. A disposable device may be preferable to a reusable one in order to avoid the question of the integrity of the device being compromised by previous use and to avoid the potential need of sterilizing the device after each use and maintaining it in controlled storage.

Despite much initial work on fabricating microneedle arrays in silicon or metals, there are significant advantages to polymeric arrays. U.S. Pat. No. 6,451,240 discloses some methods of manufacturing polymeric microneedle arrays. Arrays made primarily of biodegradable polymers also have some advantages. U.S. Pat. No. 6,945,952 and U.S. Published Patent Applications Nos. 2002/0082543 and 2005/0197308 have some discussion of microneedle arrays made of biodegradable polymers. A further description of the fabrication of a microneedle array made of polyglycolic acid is found in Jung-Hwan Park et al., “Biodegradable polymer microneedles: Fabrication, mechanics, and transdermal drug delivery,” J. of Controlled Release, 104:51-66 (2005).

Conventional micromolding techniques have been used to fabricate molds for forming microprotrusion arrays (Park et al., *Biomed Microdevices,* 2007, 9 (2): 223-234). A method for fabricating microneedles using photolithography and soft lithography techniques is described is described in U.S. Pat. No. 7,763,203. However, conventional micromolding and lithography techniques have limitations when producing complicated microstructure structures and shapes.

A method of forming microprotrusion arrays using solvent casting methods is described in U.S. Publication No. 2008/0269685, which is incorporated in its entirety herein by reference. These arrays are formed using ceramic, metal, or polymer molds where the material for the microprotrusion arrays are cast onto the molds.

Despite these efforts, there is still a need to find simpler and better methods for the manufacture of polymeric delivery systems. One problem with the present molds is that it is difficult to prepare molds having the desired shape for the microprotrusions. One particular need is for manufacture of a simple method for forming microstructure array molds. A further need is for the manufacture and use of molds that reduce or eliminate the need for extensive machining of arrays formed in the mold.

The foregoing examples of the related art and limitations related therewith are intended to be illustrative and not exclusive. Other limitations of the related art will become apparent to those of skill in the art upon a reading of the specification and a study of the drawings.

BRIEF SUMMARY

The following aspects and embodiments thereof described and illustrated below are meant to be exemplary and illustrative, not limiting in scope.

In one aspect, a method of forming a master mold is provided. In some embodiments, a master mold for use in preparing or forming a microstructure array is provided. In some embodiments, the method comprises a) forming a plurality of microstructures each comprising a shaft portion and a distal tip section in a substrate formed of a first material by a first micromachining process; b) preparing a mold of the plurality of microstructure portions formed in a) such that the mold includes the negative of the plurality of microstructure portions, wherein the mold is formed of a second material; c) electroplating a metal onto the mold, to fill cavities in the mold and to create a base layer; d) forming a proximal section for each of the microstructures in the base layer using a second micromachining process; and e) removing the second material from the metal to form a master mold. In embodiments, the second micromachining process is a mechanical micromachining process. In some embodiments, the first micromachining process comprises a photolithography process. In some embodiments, the first material is selected from silicon and a positive photoresist material. In some embodiments, the second material is a polymeric material. In some embodiments, the polymeric material is selected from the group consisting of polydimethylsiloxane (PDMS), polycarbonate, polyetherimide, polyethylene terephthalate, or mixtures thereof.

In some embodiments, the electroplating metal is selected from copper, nickel, chromium, and/or gold.

In some embodiments, a photolithography method comprises 1) applying a layer of photoresist on the first material; 2) applying a masking material onto the photoresist layer, wherein the masking material covers at least a portion or the photoresist layer; 3) curing the portion of the photoresist layer not covered by the masking material; 4) isotropic etching the substrate to create the distal tip section; 5) etching the substrate to create the shaft portion; 6) wet thermal oxidizing the microstructures; and 7) isotropic wet etching the microstructures. In embodiments, the first material is silicon. In some embodiments, the photolithography method comprises forming a layer of silicon dioxide on the silicon substrate using a thermal oxidation process prior to step 1. In some embodiments, the thermal oxidation process in step 1 is a wet thermal oxidation process. In some embodiments, the photoresist material is an epoxy-based negative photoresist. In some embodiments, the photoresist material is SU8. In some embodiments, the masking material comprises a plurality of apertures, wherein the photoresist layer exposed by the apertures is cured in step 3.

In some embodiments, the photolithography method further comprises removing the masking material and any uncured photoresist material after step 3, e.g., after curing the portion of the photoresist layer not covered by the masking material. In some embodiments, the masking material and uncured photoresist are removed using a solvent. In some embodiments, the etching is anisotropic etching, deep reactive-ion etching, and/or plasma etching. In some embodiments, plasma etching comprises a plasma gas selected from at least one of $SF_6$, carbon tetrachloride, oxygen, and $CHF_3$.

In another aspect, a method of forming a casting mold is provided. In embodiments, a negative mold of a master mold is prepared.

In another aspect, a method of preparing a microstructure array is provided. In some embodiments, the method comprises dispensing a polymer matrix solution or suspension comprising at least one therapeutic agent on a casting mold, drying the polymer matrix solution; dispensing a polymer matrix backing solution on the casting mold; drying the polymer matrix backing solution to form the microstructure array; and demolding the resulting microstructure array.

Additional embodiments of the present molds, microstructures, arrays, methods, apparatuses, devices, and the like, will be apparent from the following description, drawings, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present invention. Additional aspects and advantages of the present invention are set forth in the following description and claims, particularly when considered in conjunction with the accompanying examples and drawings.

BRIEF DESCRIPTION OF DRAWINGS

FIGS. 3A-3D are illustrations of microstructure shapes, according to some embodiments.

Figures 1A, 1B, 1C, 1D, 1E, 1F, 1G, 1H, 1I, 1J, 1K:
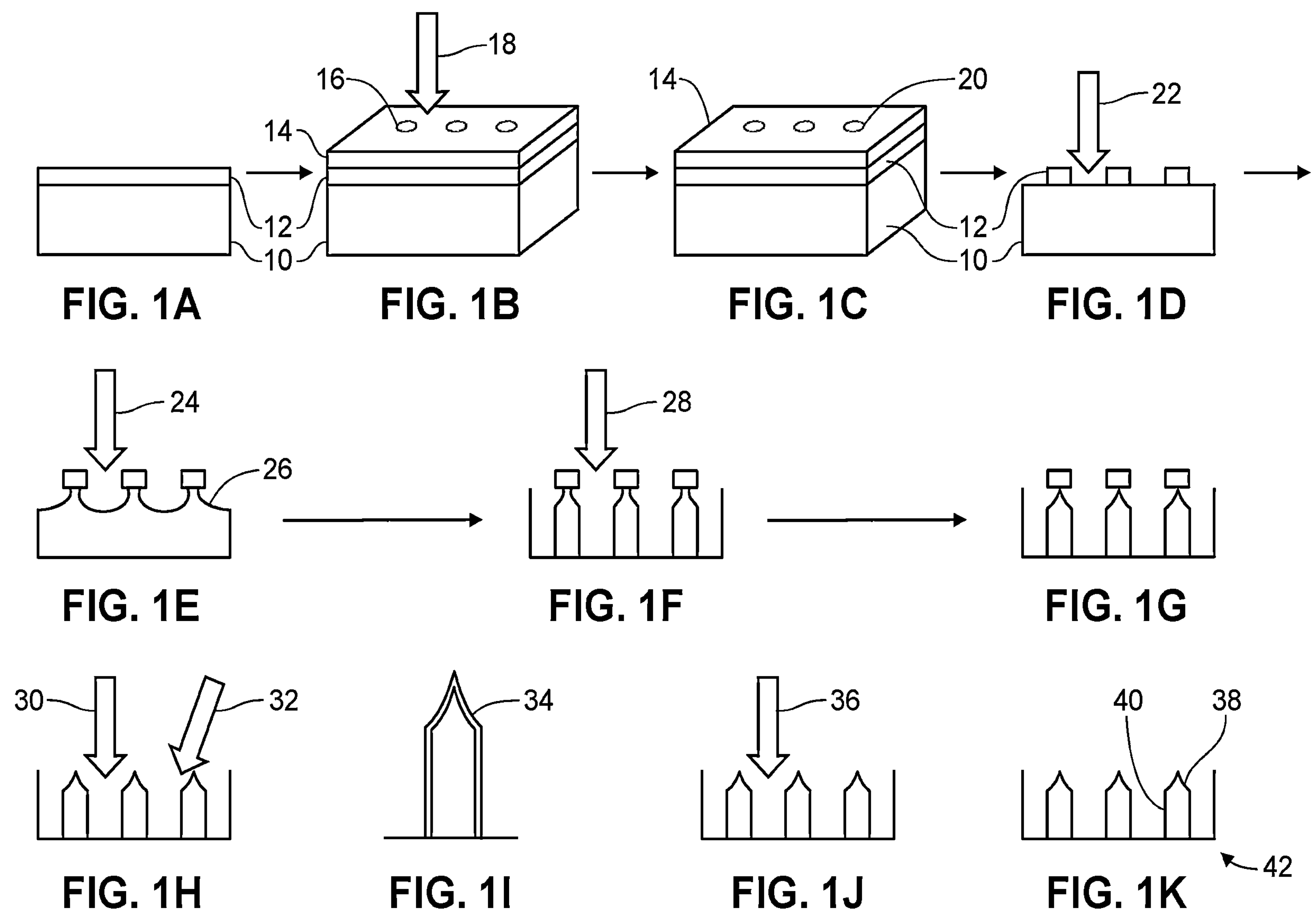
FIGS. 1A-1K are illustrations of an embodiment of a method of forming a mold useful to manufacture microstructure arrays.

It will be appreciated that the thicknesses and shapes for the various microstructures have been exaggerated in the drawings to facilitate understanding of the device. The drawings are not necessarily "to scale."

Various aspects now will be described more fully hereinafter. Such aspects may, however, be embodied in many different forms and should not be construed as limited to the embodiments set forth herein; rather, these embodiments are provided so that this disclosure will be thorough and complete, and will fully convey its scope to those skilled in the art.

DETAILED DESCRIPTION

The practice of the present disclosure will employ, unless otherwise indicated, conventional methods of chemistry, biochemistry, and pharmacology, within the skill of the art. Such techniques are explained fully in the literature. See, e.g.; A. L. Lehninger, *Biochemistry* (Worth Publishers, Inc., current addition); Morrison and Boyd, *Organic Chemistry* (Allyn and Bacon, Inc., current addition); J. March, *Advanced Organic Chemistry* (McGraw Hill, current addition); *Remington: The Science and Practice of Pharmacy*, A. Gennaro, Ed., 20$^{th}$ Ed.; *Goodman & Gilman The Pharmacological Basis of Therapeutics*, J. Griffith Hardman, L. L. Limbird, A. Gilman, 10$^{th}$ Ed.

Where a range of values is provided, it is intended that each intervening value between the upper and lower limit of that range and any other stated or intervening value in that stated range is encompassed within the disclosure. For example, if a range of 1 μm to 8 μm is stated, it is intended that 2 μm, 3 μm, 4 μm, 5 μm, 6 μm, and 7 μm are also explicitly disclosed, as well as the range of values greater than or equal to 1 μm and the range of values less than or equal to 8 μm.

As used in this specification, the singular forms "a," "an," and "the" include plural referents unless the context clearly dictates otherwise. Thus, for example, reference to "a polymer" includes a single polymer as well as two or more of the same or different polymers; reference to "an excipient" includes a single excipient as well as two or more of the same or different excipients, and the like.

In describing and claiming the present invention, the following terminology will be used in accordance with the definitions described below.

The word "about" when immediately preceding a numerical value means a range of plus or minus 10% of that value, e.g., "about 50" means 45 to 55, "about 25,000" means 22,500 to 27,500, etc., unless the context of the disclosure indicates otherwise, or is inconsistent with such an interpretation. For example in a list of numerical values such as "about 49, about 50, about 55, "about 50" means a range extending to less than half the interval(s) between the preceding and subsequent values, e.g., more than 49.5 to less than 52.5. Furthermore, the phrases "less than about" a value or "greater than about" a value should be understood in view of the definition of the term "about" provided herein.

The terms "microprotrusion", "microprojection", "microstructure" and "microneedle" are used interchangeably herein to refer to elements adapted to penetrate or pierce at least a portion of the stratum corneum or other biological membrane. For example, illustrative microstructures may include, in addition to those provided herein, microblades as described in U.S. Pat. No. 6,219,574, edged microneedles as described in U.S. Pat. No. 6,652,478, and microprotrusions as described in U.S. Patent Publication No. U.S. 2008/0269685.

The term "microstructure array" for purposes herein is intended to denote a two-dimensional or a three-dimensional arrangement of microstructures, microprotrusions, microprojections, or microneedles. The arrangement may be regular according to a repeating geometric pattern or it may be irregular. A typical "microstructure array", "microprojection array", or "microneedle array" comprises microstructures, microprojections, or microneedles projecting from a base or substrate of a particular thickness, which may be of any shape, for example square, rectangular, triangular, oval, circular, or irregular. An array typically comprises a plurality of microstructures, microprojections, or microneedles. The microstructures, microprojections, or microneedles themselves may have a variety of shapes. While an array could be pressed by hand into skin, a variety of devices may be used to hold the array as it is being applied and/or to facilitate, in one way or another, the process of application of the array to the skin or other biological membrane. Such devices may broadly be referred to as "applicators." Applicators may for example reduce the variations in force, velocity, and skin tension that occur when an array is pressed by hand into the skin. Variations in force, velocity and skin tension can result in variations in permeability enhancement.

In discussing the applicators and arrays described herein, the term "downward" is sometimes used to describe the direction in which microstructures are pressed into skin, and "upward" used to describe the opposite direction. However, those of skill in the art will understand that the applicators can be used where the microstructures are pressed into skin at an angle to the direction of the earth's gravity, or even in a direction contrary to that of the earth's gravity. In many applicators, the energy for pressing the microstructures is provided primarily by an energy-storage member and so efficiency is not much affected by the orientation of the skin relative to the earth's gravity.

"Biodegradable" refers to natural or synthetic materials that degrade enzymatically, non-enzymatically or both to produce biocompatible and/or toxicologically safe by-products which may be eliminated by normal metabolic pathways. The term "biodegradable" is intended to include the processes of erosion, dissolution, disintegration, and degradation, as well as to include those materials that are often referred to as being bioerodible or biodegradable.

"Non-biodegradable" refers to natural or synthetic materials that do not appreciably degrade when inserted into and/or contacted with skin, mucosa, or other biological membrane for a period of time associated with use of microstructure arrays. In some embodiment, "non-biodegradable" refers to materials that do not appreciably degrade when inserted into and/or contacted with skin, mucosa or another biological membrane for a period of at least about 5 minutes, about 10 minutes, about 15 minutes, about 20 minutes, about 30 minutes, about an hour or more. The term "non-biodegradable" is also intended to include the processes of erosion, dissolution, and disintegration.

"Optional" or "optionally" means that the subsequently described circumstance may or may not occur, so that the description includes instances where the circumstance occurs and instances where it does not.

In this application reference is often made for convenience to "skin" as the biological membrane which the microstructures penetrate. It will be understood by persons of skill in the art that in most or all instances the same inventive principles apply to the use of microstructures to penetrate other biological membranes such as, for example, those which line the interior of the mouth or biological membranes which are exposed during surgery.

"Substantially" or "essentially" means nearly totally or completely, for instance, 90-95% or greater of some given quantity.

"Transdermal" refers to the delivery of an agent into and/or through the skin for local and/or systemic therapy. Administration through other biological membranes, such as those which line the interior of the mouth, gastro-intestinal tract, blood-brain barrier, or other body tissues or organs or biological membranes which are exposed or accessible during surgery or during procedures such as laparoscopy or endoscopy, are also contemplated as surfaces for which the microstructures described herein find use.

A material that is "water-soluble" intends a material soluble or substantially soluble in aqueous solvents, such that the material dissolves into, within or below the skin or other membrane which is substantially aqueous in nature.

The compositions of the present disclosure can comprise, consist essentially of, or consist of, the components disclosed.

I. Methods of Making Microstructure Array Molds

Before describing the methods of manufacture in detail, it is to be understood that the methods are not limited to specific solvents, materials, or device structures, as such may vary. It is also to be understood that the terminology used herein is for the purpose of describing particular embodiments only, and is not intended to be limiting.

In general, an array of microstructures, or a portion thereof, is formed in a material such as silicon or photoresist using semiconductor microfabrication techniques. Negative molds of the microstructure array (portions) may be formed of silicones or other suitable materials. The microfabricated portions are removed and electroforming techniques are used to fill the cavities with a suitable metal. An additional section of metal is electroformed to create a base for preparing the proximal portion of the microstructures. The additional section is micromachined to create the desired shape for the proximal portion of the microstructures. This positive mold may be used as a master mold suitable for use in creating one or more negative molds. These negative molds may then be used in casting microstructure arrays for use.

The molds used to form the arrays herein can be made using a variety of methods and materials. In one general method, a master mold for use in making microstructure arrays is prepared. The master mold may be formed by creating a positive master mold, which is then used to form negative molds. The master mold may be used to prepare casting molds for preparing the microstructure arrays for use. In an embodiment, the method comprises a hybrid method that comprises (i) forming a positive mold of at least a portion of the microstructure structure, (ii) forming a negative mold from the positive mold of (i), (iii) preparing a second positive mold including the microstructure structure; and (iv) micromachining the second positive mold to form the master mold with the microstructures having the desired shape. In one embodiment, the step identified by (i), forming a positive mold of at least a portion of the microstructure structure, comprises forming a positive mold of the distal tip and of the shaft portion of a microstructure. In one embodiment, the step identified by (iii), preparing a second positive mold including the microstructure structure, comprises electroforming the negative mold to fill the cavities of the positive mold and to create a base layer that extends from the negative mold. In one embodiment, the step identified by (iv), micromachining the second positive mold, comprises micromachining the base layer that extends from the negative mold into a funnel shape or other shape that corresponds to the desired shape of the base portion of each microstructure.

In general, the method of fabricating the mold is a hybrid method involving micromachining, lithography and mold casting to form a master mold, casting molds and/or a microstructure array. In general, microfabrication methods such as semiconductor microfabrication methods are used to form at least a distal portion of the microstructure mold. The semiconductor microfabrication is used to form at least the distal portion or sharp tip of the microstructures. One such microfabrication method is shown generally in FIGS. 1A-1K. In general, semiconductor microfabrication methods use combinations of photolithography and etching to create a desired shape. It will be appreciated that other methods and/or materials as known and/or used in the fabrication of microelectronics including, but not limited to, semiconductor fabrication may be used or incorporated into the methods described below.

With reference to FIGS. 1A-1K, an exemplary semiconductor micromachining process is shown for preparing the distal portion or distal tip of the microstructure master mold. It will be appreciated that other steps or steps in a different order may be used to create the microstructure distal portion or tip.

A substrate 10 formed of a suitable material is provided. The substrate may be formed of any material suitable for use with photolithography techniques. In non-limiting embodiments, the substrate is formed from silicon or a positive photoresist material. In some embodiments, the substrate is formed from a glass including, but not limited to a borosilicate glass such as PYREX® (Corning) or a sapphire glass. In one embodiment, positive photoresist materials become soluble to a photoresist stripper or developer when exposed to light or a particular wavelength of light. As an initial step, the substrate may be cleaned using any methods known in the art. It will be appreciated that the method of cleaning the substrate may depend on the composition of the substrate. In one embodiment where the substrate is formed of silicon, the substrate may be cleaned by the RCA clean method as known in the art. In embodiments, the substrate may be treated or coated with one or more materials. For example, the substrate may be coated with a material that adjusts or aids the photolithography or etching processes. In one embodiment, the substrate is coated with an antireflective coating or a coating that adjusts or improves the angle of light used in subsequent steps. In another embodiment, where the substrate is a silicon substrate, a layer of oxide such as silicon dioxide may be formed on the substrate 10 by a suitable process prior to photoresist coating. One exemplary process is a thermal oxidation procedure such as wet thermal oxidation.

The microstructure tips may be formed using any suitable photolithography techniques as known in the art. In one embodiment, a layer of negative photoresist 12 is added to the upper or an exposed surface of the substrate 10 (step (a)). One suitable photoresist is an epoxy-based photoresist, such as SU-8 (Microchem). As a photoresist, SU-8 may produce a film thickness of 30 microns or greater (e.g. about 0.5 μm to >200 μm thickness in a single coating). It will be appreciated that other materials as known in the art may be used as the photoresist. Further, other photoresist materials or otherwise light and/or radiation sensitive materials may be used to create a thickness of photoresist on the substrate of less than or greater than about 30 microns. The photoresist may be applied by spin-coating or may be otherwise applied or spread over the substrate to a desired thickness. In embodiments, the photoresist may be deposited or applied to a thickness ranging from about 1 micron to about 300 microns, or from about 5 microns to about 500 microns, or from about 10 microns to about 275 microns.

A masking material 14 is placed over at least a portion of the photoresist material (step (b)). Any suitable masking material as known in the art may be used. In embodiments, the masking material may be photoresist that has been patterned using photolithography techniques. In other embodiments, the masking material may be a coated glass or quartz plate with a desired pattern imprinted. In other embodiments, the masking material may be a coating as known in the art including, but not limited to, silicon dioxide or $Si_3N_4$. The masking material may include one or more apertures, openings, patterns or features that are used to create at least a portion of the microstructure shape. In the example shown in FIG. 1B, the masking material includes a plurality of openings or apertures 16 that approximately correspond to the diameter of the microstructures to be formed in the substrate. In some embodiments, the masking material is a stencil, a planar sheet of material with desired shapes and patterns etched out of the sheet. It will be appreciated that the apertures or openings in the masking material may be any desired shape but will generally correspond to the shape of the outer edge or a cross-section of the microstructures formed. For example, masks having polygonal apertures or openings (e.g. square or rectangular) may result in microstructures having, for example, a square, rectangular, or diamond shape or cross-section. The photoresist is cured 18 such that the photoresist present below and exposed by the apertures or openings 20 is cured (step (c)). The photoresist may be cured by any suitable method or methods as known in the art. Exemplary methods of curing the photoresist include, but are not limited to exposure to radiation, including but not limited to UV or near-UV radiation, deep UV radiation, e-beam radiation, or x-ray radiation. Where SU-8 photoresist is used, the photoresist may be cured by exposing the photoresist to light in the near UV spectrum (e.g. 350-400 nm).

The masking material and the uncured photoresist material are removed by suitable means known in the art 22 leaving the substrate 10 and the cured photoresist 12 (step (d)). In embodiments, a developer, stripper and/or other solvent as known in the art is used to remove the uncured photoresist. In some exemplary embodiments, the developer is specific for the photoresist such as the SU-8 developer available from MicroChem. In other embodiments, the developer may be a solvent-based developer including, but not limited to ethyl lactate or diacetone alcohol. The solvent is applied until dissolution of the uncured photoresist. Solvent may be applied by any suitable means. In some non-limiting embodiments, solvent is applied by at least one of bath immersing the substrate, spray-coating the substrate, and/or direct dispensing of solvent over the top surface of the substrate. Generally, the substrate is incubated with the solvent for a period of time to permit selective dissolution of the photoresist material. In other embodiments, the photoresist may be removed by an oxygen plasma etch process.

The substrate is etched using one or more etching steps. In embodiments, an isotropic etchant 24 is initially used to produce an inward portion 26 of the microstructure distal end and/or distal tip (step (e)). In general, isotropic etchants etch uniformly in all directions so that a portion of the substrate positioned directly under the cured photoresist is etched away in both the lateral as well as the vertical direction. Knowing the rate of etching for the etchant, one skilled in the art can formulate the appropriate time of etchant application to achieve a desired shape. The isotropic etch may be a wet etch (e.g. via immersion in a liquid etchant) and/or a dry (plasma) etch as known in the art. In one embodiment, an isotropic wet etch is followed by an isotropic plasma etch using, for example, $SF_6$, carbon tetrachloride, oxygen or $CHF_3$ or a mixture of any of these gases.

In embodiments, the substrate is further subjected to etching using an anisotropic etchant (step (f)). In one embodiment, the substrate is subjected to deep reactive ion etching (DRIE). Antistrophic etching is directionally dependent. Thus, the angle or orientation of the etchant source with respect to the surface of the substrate determines the angle of the etch. For example, as shown in FIG. 1F, a DRIE etchant 28 is applied at an angle of about 90° to the surface of the substrate. The resulting etch creates structures in the substrate having a wall that is about 90° to the bottom surface of the substrate. It will be appreciated that the angle of application of the etchant may be adjusted to create microstructures with desired configurations and structures. The cured photoresist material is removed by any immersion and/or soaking of the substrate with a suitable solvent or stripper (liquid) suitable solvent or stripper as known in the art (step (g)). It will be appreciated that the solvent or stripper preferably does not significantly affect the shape of the microstructures formed in the substrate. In some embodiments, the cured photoresist may be removed by "dry" methods via plasma treatment.

The microstructures are finished using suitable means as known in the art. The finishing steps serve to refine and define the desired shape of the microstructures for the mold as well as the arrays formed therefrom. The finishing steps may include refinement of the microstructure shapes, which includes adjusting angles for the microstructures and/or finishing a surface of at least a portion of the microstructures. Some exemplary etching steps for finishing are shown in steps (h)-(j) of FIGS. 1H-1J. It will be appreciated that one or more additional finishing steps may be used. It will further be appreciated that not all of the finishing steps depicted in FIGS. 1H-1J need be used. In one embodiment one or more of a plasma etch, a wet thermal oxidation step, and/or an isotropic wet etch may be used for finishing the microstructure surfaces (steps (h)-(j)). In step (h), a plasma etch is performed as described above using a suitable gas or mixture of gases including, but not limited to, $SF_6$. This plasma etch is used to finish the surface and/or correct the angles for the distal tip of the microstructures. When using an anisotropic etch, it will be appreciated that the flow of the plasma may be adjusted to create the desired angle and/or shape as depicted by 30 and 32. As seen in steps (i)-(j), wet thermal oxidation is followed by an isotropic etch to create a smooth surface for the microstructures and/or the sharp tip. Wet thermal oxidation forms a layer of silicon dioxide 34 in the outer surface of the silicon substrate. This layer may be easily removed leaving a smooth surface. One exemplary method of removing the silicon dioxide layer is isotropic wet etching 36 as shown in step (j). Any suitable wet etching process as known in the art may be used. Wet etching typically involves contacting the material with a chemical etchant. In an embodiment, the chemical etchant is an acid including, but not limited to, hydrofluoric acid or phosphoric acid.

As seen in FIG. 1K, the resulting microstructure structures 42 have a shaft 40 and sharpened distal tip 38. The shaft length should be of sufficient length to allow for penetration of the skin to a desired depth.

Figure 2:
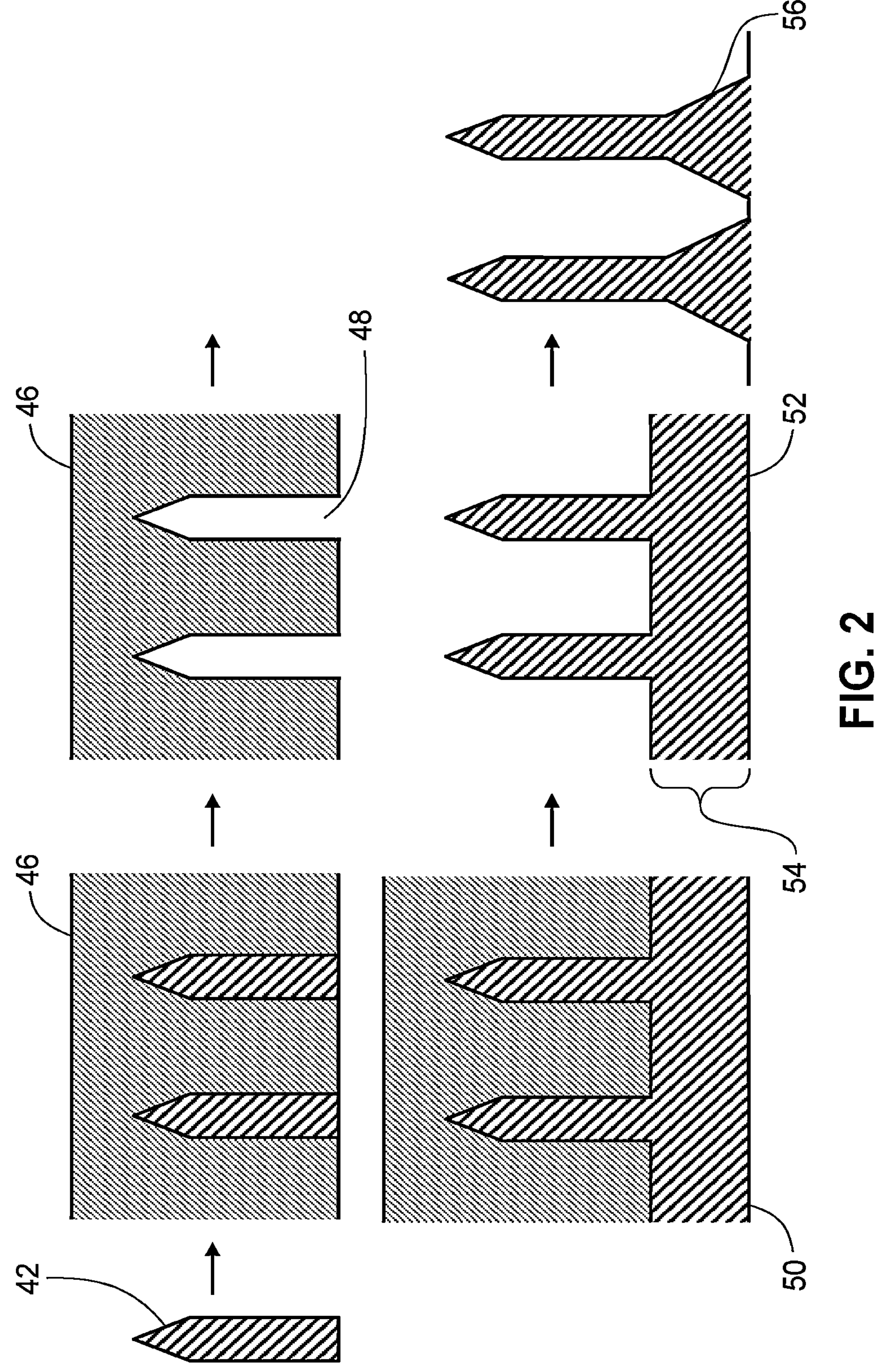
FIG. 2 is an illustration of an embodiment of a method of forming a mold useful to manufacture microstructure arrays.

As seen in FIG. 2, the positive mold with microstructure structures 42 formed as above is then used to form a negative mold 46. The negative mold may be formed by any suitable methods and/or materials as known in the art. In one embodiment, the negative mold is formed by inserting the microstructure structures into a negative mold material. In other embodiments, the negative mold is formed by coating the positive mold microstructure structures with a negative mold material. In embodiments, the negative mold material is a polymer. In embodiments, the polymer is a soluble polymer. In embodiments, the polymer is a silicone polymer. In particular embodiments, the polymer is selected from polydimethylsiloxane (PDMS) and polylactic-co-glycolyic acid (PLGA). The microstructures are removed leaving the polymeric negative mold 46 with cavities 48 in the shape of the microstructure structures 42 of the positive mold.

With continued reference to FIG. 2, negative mold 46 is then used to form a second positive mold, also referred to herein as a master mold, formed of a durable material, such as a metal. In embodiments, negative mold 46 is coated with a suitable durable material 50. In non-limiting embodiments, the durable material is a metal which is selected from copper, gold, nickel, chromium, rhodium, platinum, or alloys thereof. The metal may be coated, applied, or plated onto the negative mold using any suitable methods including, but not limited to, electroplating, electron beam deposition, and sputter coating. An excess portion of metal is applied as shown by 52 to create a base or proximal region of the microstructures. That is, the durable material is deposited in an amount sufficient to entirely fill the cavities in the negative mold and to form a layer or base layer 52 on the negative mold. The base may be any suitable thickness 54 as needed for forming the proximal portion of the microstructures. The metal positive mold is removed from the negative mold 46. At this point, the positive mold includes the shaft and distal tip of the microstructures with a slab or base layer 52 having thickness 54. The base 52 is then machined using suitable mechanical machining methods as known in the art to create a desired shape of the proximal portion 56 of the microstructures. In preferred embodiments, the proximal portion 56 has a funnel or pyramidal shape. Any remaining material from the negative mold 46 is removed by a suitable solvent, such as methylene chloride.

In one exemplary embodiment, a negative mold is formed from a silicone such as polydimethylsiloxane. The negative mold is typically formed casting a liquid mold material over the positive master array. The negative mold casting solution material is allowed to dry and harden. When the hardened material is peeled or removed from the positive mater, created is a mold comprising cavities corresponding to the microstructures of the positive master array. It will be appreciated that the molds suitable for use in the present methods may be prepared according to other methods.

One exemplary master array mold includes a plurality of microstructures projections having a height of about 100-500 μm. In general, the master array mold includes a plurality of microstructures having a height of at least about 100 μm, at least about 150 μm, at least about 200 μm, at least about 250 μm, or at least about 300 μm. In general it is also preferred that the microstructures of the master array mold have a height of no more than about 1 mm, no more than about 500 μm, no more than about 300 μm, or in some cases no more than about 200 μm or 150 μm. In embodiments, the microstructures of the master array mold have a height of at least about 50-500 μm. In other embodiments, the microstructures of the master array mold have a height of at least about 100-500 μm, 100-400 μm, 100-300 μm, 100-200 μm, 100-150 μm, 150-500 μm, 150-400 μm, 150-300 μm, 150-200 μm, 200-500 μm, 200-400 μm, 200-300 μm, 300-500 μm, 300-400 μm, or 400-500 μm. It will be appreciated that the microstructures within an array may have a range of heights. The microstructures of the array master mold may have any suitable shape including, but not limited to polygonal or cylindrical. Particular embodiments include a combination of funnel and cylinder shapes having a funnel tip and a cylindrical base, and a cone with a polygonal bottom, for example hexagonal or rhombus-shaped. Some particular shapes are shown in FIGS. 3A-3D. Other possible microstructure shapes are shown, for example, in U.S. Published Patent App. 2004/0087992 and in U.S. Application No. 2014/0180201. In one embodiment, a mold is created to form microstructures shaped like an obelisk, where a distal portion of the microneedle shaft is a pyramidion with four angled faces joining and tapering to form a tip that penetrates the skin. The needle shaft that bears the pyramidion has four planar or flat sides.

In some particular embodiments, the master array includes a plurality of microstructures having a height of about 200 μm, a base of about 70 μm, and spacing between the projections of about 200 μm. In another exemplary embodiment, the master array includes a plurality of hexagonal or other polygonal shaped projections having a height of about 200 μm, a base of about 70 μm, and spacing between the projections of about 400 μm. In yet another embodiment, the master array includes a plurality of cylindrical shaped projections having a height of about 400 μm, a diameter of about 100 μm, and spacing between the projections of about 200 μm. It will be appreciated that the cylindrical shaped projections may have a funnel shaped, pointed, or sharp distal end.

The microstructures of the master mold may be spaced about 0-500 μm apart. In specific, but not limiting embodiments, the microstructures of the master mold are spaced about 0 μm, about 50 μm, about 100 μm, about 150 μm, about 200 μm, about 250 μm, about 300 μm, about 350 μm, about 400 μm, about 450 μm, or about 500 μm apart. The space between the microstructures may be measured from the base of the microstructures (base to base) or from the tip (tip to tip). The spacing of the microstructures of the master mold may be regular or irregular.

This master mold may then be used to form multiple negative molds of any suitable material. These negative molds may be used in in the manufacture of microstructure arrays where each microstructure comprises a therapeutic agent to be administered to a subject for treatment. In one embodiment, the negative mold is referred to as a casting mold as it received a casting solution or suspension comprised of the therapeutic agent. An advantage of this method for providing casting molds is that the casting molds do not require machining to form the desired shapes of the distal and proximal portions of the microstructures. The casting molds may be formed of any suitable material, including polymers and silicon. In one embodiment, the polymer is PDMS, which has the advantages of biocompatibility, viscoelasticity, high chemical inertness, and ability to adhere to metals, among others. In other embodiments, the casting mold is formed of any natural or synthetic rubber (e.g., isoprene, natural rubber, butyl rubber) or polyurethane.

II. Methods of Making Microstructure Arrays

The methods and resulting molds described in Section I above may be used in fabricating microstructure arrays. Exemplary methods are described in U.S. Publication No. 2013/0292868 and 2014/0272101, which are incorporated herein by reference, wherein a casting solution or suspension is deposited on a negative casting mold. In one exemplary method, a microstructure array is prepared by a casting a polymer matrix solution (or suspension) on or in a negative casting mold. The solution is dried and a backing polymer solution (or suspension) is cast on or in the negative casting mold. The backing solution is dried. After drying, the casting mold is removed. The microstructures formed from the dried polymer matrix solution and the dried backing solution result in an array of two-layer microstructures, particularly in embodiments where the two solutions are different.

In one embodiment, a casting solution is formed by dissolving or suspending one or more therapeutic agents, active agents, drugs, active pharmaceutical ingredients (APIs), or other substances to be delivered to a subject and one or more polymers in a solvent to form a polymer matrix solution or suspension. The terms active agent, therapeutic agent, agent, drug, and API are used interchangeably herein and discussion or reference to one is intended to include and apply to each and all terms. In one embodiment, the casting solution is formed by dissolving or suspending at least one agent and one or more polymers in an aqueous buffer or solvent to form a solution or suspension comprising the active agent and the polymer. In another embodiment, at least one active agent is dissolved or suspended in a solvent to form an active agent solution or suspension. At least one polymer is separately dissolved in a solvent to form a polymer solution or suspension. The suspension may be a liquid in liquid suspension or a solid in liquid suspension depending on the nature of the active agent and/or polymer. The solvent(s) used for the active agent solution and the polymer solution may be the same or different. The active agent solution and the polymer solution are mixed to form a polymer matrix solution or suspension. It will further be appreciated that a solvent mixture may be used to dissolve or suspend the active agent and/or polymer.

Casting solvents are, in one embodiment, preferably aqueous solvents. Suitable aqueous solvents include, but are not limited to, water and mixtures of water and alcohols (for example, C1 to C8 alcohols such as propanol and butanol) and/or alcohol esters. In other embodiments, the solvents are non-aqueous. Suitable non-aqueous solvents include, but are not limited to, esters, ethers, ketones, nitrites, lactones, amides, hydrocarbons and their derivatives as well as mixtures thereof. In other non-limiting embodiments, the solvent is selected from acetonitrile (ACN), dimethyl sulfoxide (DMSO), water, or ethanol. It will be appreciated that the choice of solvent may be determined by one or more properties of the active agent and/or polymer. It will further be appreciated that the casting solvent may comprise a mixture of solvents.

Any suitable drug, therapeutic agent, API, or other active agent may be dissolved or suspended in the solvent. The present arrays are suitable for a wide variety of substances or agents. Suitable active agents that may be administered include the broad classes of compounds such as, by way of illustration and not limitation: analeptic agents; analgesic agents; antiarthritic agents; anticancer agents, including antineoplastic drugs; anticholinergics; anticonvulsants; antidepressants; antidiabetic agents; antidiarrheals; antihelminthics; antihistamines; antihyperlipidemic agents; antihypertensive agents; anti-infective agents such as antibiotics, antifungal agents, antiviral agents and bacteriostatic and bactericidal compounds; antiinflammatory agents; antimigraine preparations; antinauseants; antiparkinsonism drugs; antipruritics; s; antipsychotics; antipyretics; antispasmodics; antitubercular agents; antiulcer agents; anxiolytics; appetite suppressants; attention deficit disorder and attention deficit hyperactivity disorder drugs; cardiovascular preparations including calcium channel blockers, antianginal agents, central nervous system agents, beta-blockers and antiarrhythmic agents; caustic agents; central nervous system stimulants; cough and cold preparations, including decongestants; cytokines; diuretics; genetic materials; herbal remedies; hormonolytics; hypnotics; hypoglycemic agents; immunosuppressive agents; keratolytic agents; leukotriene inhibitors; mitotic inhibitors; muscle relaxants; narcotic antagonists; nicotine; nutritional agents, such as vitamins, essential amino acids and fatty acids; ophthalmic drugs such as antiglaucoma agents; pain relieving agents such as anesthetic agents; parasympatholytics; peptide drugs; proteolytic enzymes; psychostimulants; respiratory drugs, including antiasthmatic agents; sedatives; steroids, including progestogens, estrogens, corticosteroids, androgens and anabolic agents; smoking cessation agents; sympathomimetics; tissue-healing enhancing agents; tranquilizers; vasodilators including general coronary, peripheral and cerebral; vessicants; and combinations thereof.

In embodiments, the active agent is a biological agent including, but not limited to peptides, polypeptides, proteins, or nucleic acids (e.g. DNA or RNA). In one embodiment, the active agent is a polypeptide such as human parathyroid hormone (e.g. hPTH(1-34)), a protein such as human growth hormone, or an antibody. Examples of peptides and proteins which may be used with the microstructure arrays include, but are not limited to, parathyroid hormone (PTH), oxytocin, vasopressin, adrenocorticotropic hormone (ACTH), epidermal growth factor (EGF), prolactin, luteinizing hormone, follicle stimulating hormone, luliberin or luteinizing hormone releasing hormone (LHRH), insulin, somatostatin, glucagon, interferon, gastrin, tetragastrin, pentagastrin, urogastrone, secretin, calcitonin, enkephalins, endorphins, kyotorphin, taftsin, thymopoietin, thymosin, thymostimulin, thymic humoral factor, serum thymic factor, tumor necrosis factor, colony stimulating factors, motilin, bombesin, dinorphin, neurotensin, cerulein, bradykinin, urokinase, kallikrein, substance P analogues and antagonists, angiotensin II, nerve growth factor, blood coagulation factors VII and IX, lysozyme chloride, renin, bradykinin, tyrocidin, gramicidines, growth hormones, melanocyte stimulating hormone, thyroid hormone releasing hormone, thyroid stimulating hormone, pancreozymin, cholecystokinin, human placental lactogen, human chorionic gonadotropin, protein synthesis stimulating peptide, gastric inhibitory peptide, vasoactive intestinal peptide, platelet derived growth factor, growth hormone releasing factor, bone morphogenic protein, and synthetic analogues and modifications and pharmacologically active fragments thereof. Peptidyl drugs also include synthetic analogs of LHRH, e.g., buserelin, deslorelin, fertirelin, goserelin, histrelin, leuprolide (leuprorelin), lutrelin, nafarelin, tryptorelin, and pharmacologically active salts thereof. Administration of oligonucleotides is also contemplated, and includes DNA and RNA, other naturally occurring oligonucleotides, unnatural oligonucleotides, and any combinations and/or fragments thereof. Therapeutic antibodies include Orthoclone OKT3 (muromonab CD3), ReoPro (abciximab), Rituxan (rituximab), Zenapax (daclizumab), Remicade (infliximab), Simulect (basiliximab), Synagis (palivizumab), Herceptin (trastuzumab), Mylotarg (gemtuzumab ozogamicin), CroFab, DigiFab, Campath (alemtuzumab), and Zevalin (ibritumomab tiuxetan).

In other embodiments, at least a portion of the distal layer comprises an agent suitable for use as a prophylactic and/or therapeutic vaccine. In an embodiment, the vaccine comprises an antigen epitope conjugated on or to a carrier protein. It will be appreciated that vaccines may be formulated with our without an adjuvant. Suitable vaccines include, but are not limited to, vaccines for use against anthrax, diphtheria/tetanus/pertussis, hepatitis A, hepatitis B, Haemophilus influenzae type b, human papillomavirus, influenza, Japanese encephalitis, measles/mumps/rubella, meningococcal diseases (e.g., meningococcal polysaccharide vaccine and meningococcal conjugate vaccine), pneumococcal diseases (e.g., pneumococcal polysaccharide vaccine and meningococcal conjugate vaccine), polio, rabies, rotavirus, shingles, smallpox, tetanus/diphtheria, tetanus/diphtheria/pertussis, typhoid, varicella, and yellow fever.

In another embodiment, at least a portion of the distal layer comprises an agent suitable for veterinary uses. Such uses include, but are not limited to, therapeutic and diagnostic veterinary uses.

Polymers for use in the methods are typically biocompatible. In one embodiment, at least some of the polymers are biodegradable.

In an embodiment, the polymer is a structure-forming polymer. In an embodiment, the polymer is a hydrophilic water soluble polymer. Suitable polymers are known in the art and described, for example, in U.S. Patent Application No. 2008/0269685. Exemplary biocompatible, biodegradable, or bioerodible polymers include poly (lactic acid) (PLA), poly(glycolic acid) (PGA), poly(lactic acid-co-glycolic acid)s (PLGAs), polyanhydrides, polyorthoesters, polyetheresters, polycaprolactones (PCL), polyesteramides, poly(butyric acid), poly(valeric acid), polyvinylpyrrolidone (PVP), polyvinyl alcohol (PVA), polyethylene glycol (PEG), block copolymers of PEG-PLA, PEG-PLA-PEG, PLA-PEG-PLA, PEG-PLGA, PEG-PLGA-PEG, PLGA-PEG-PLGA, PEG-PCL, PEG-PCL-PEG, PCL-PEG-PCL, copolymers of ethylene glycol-propylene glycol-ethylene glycol (PEG-PPG-PEG, trade name of Pluronic® or Poloxamer®), block copolymers of polyethylene glycol-poly (lactic acid-co-glycolic acid) (PLGA-PEG), dextran, hetastarch, tetrastarch, pentastarch, hydroxyethyl starches, cellulose, hydroxypropyl cellulose (HPC), sodium carboxymethyl cellulose (Na CMC), thermosensitive HPMC (hydroxypropyl methyl cellulose), polyphosphazene, hydroxyethyl cellulose (HEC), polysaccharides, polyalcohols, gelatin, alginate, chitosan, hyaluronic acid and its derivatives, collagen and its derivatives, polyurethanes, and copolymers and blends of these polymers. One hydroxyethyl starch may have a degree of substitution of in the range of 0-0.9. An exemplary polysaccharide is dextran including dextran 70, dextran 40, and dextran 10.

The casting solution may further include one or more excipients dissolved or suspended in the buffer or solvent. Suitable excipients include, but are not limited to, one or more stabilizers, plasticizers, surfactants, and/or anti-oxidants.

In one embodiment one or more sugars is added to the casting solution. Sugars can stabilize the active ingredient and/or plasticize at least one of the polymers. Sugars may also be used to affect, moderate, or regulate degradation of the polymer(s). Exemplary sugars include, but are not limited to, dextrose, fructose, galactose, maltose, maltulose, iso-maltulose, mannose, lactose, lactulose, sucrose, and trehalose, and sorbitol. In other embodiments, a sugar alcohol as known in the art is included in the casting solution. Exemplary sugar alcohols include, but are not limited to, lactitol, maltitol, sorbitol, and mannitol. Cyclodextrins can also be used advantageously in microstructure arrays, for example α, β, and γ cyclodextrins. Exemplary cyclodextrins include hydroxypropyl-β-cyclodextrin and methyl-β-cyclodextrin. In other embodiments, where Dextran, hetastarch and/or tetrastarch is used as a polymer in the casting solution, sorbitol may preferably be included in the casting solution. In this embodiment, sorbitol may not only stabilize the active agent, but also plasticize the polymer matrix, which reduces brittleness. The biodegradability or dissolvability of the microstructure array may be facilitated by the inclusion of sugars. Sugars and sugar alcohols may also be helpful in stabilization of peptides, proteins, or other biological active agents and in modifying the mechanical properties of the microstructures by exhibiting a plasticizing-like effect. Where the active agent is a biological agent including, but not limited to, peptides, proteins, and antibodies, one or more sugars or sugar alcohols may be used in the casting solution as a stabilizing agent. The sugar may be added to (i) the therapeutic agent solution or suspension, (ii) the polymer solution or suspension, or (iii) the polymer matrix solution or suspension once (i) and (ii) have been mixed.

One or more surfactants may be added to the casting solution to change the solutions' surface tension and/or reduce the hydrophobic interactions of proteins. Any suitable surfactant as known in the art may be used. Exemplary surfactants include, but are not limited to, emulsifiers such as Polysorbate 20 and Polysorbate 80.

One or more antioxidants may be added to the casting solution. Any suitable antioxidant as known in the art may be used. Exemplary antioxidants include, but are not limited to, methionine, cysteine, D-alpha tocopherol acetate, EDTA, and vitamin E.

In one embodiment, an optional backing layer, base layer, or basement is further cast on the mold. A liquid backing formulation is dispensed on the mold or into the cavities. The liquid backing formulation is typically prepared by dissolving or suspending one or more polymers in a suitable solvent. In a preferred embodiment, the one or more polymers are biocompatible. Typically, but not always, the polymers are non-biodegradable. In another embodiment, the backing formulation may comprise one or more biodegradable and/or non-biodegradable polymers. Suitable biodegradable polymers are described above. Suitable non-biodegradable polymers are known in the art and include, but are not limited to, amphiphilic polyurethanes, polyether polyurethane (PEU), polyetheretherketone (PEEK), poly (lactic-co-glycolic acid) (PLGA), polylactic acid (PLA), polyethylene terephthalate, polycarbonate, acrylic polymers such as those sold under the trade name Eudragit®, polyvinylpyrrolidones (PVP), polyamide-imide (PAI), and/or co-polymers thereof. Further suitable polymers are described in U.S. Pat. No. 7,785,301, which is incorporated herein in its entirety. In another embodiment, the backing layer is an adhesive layer. One suitable adhesive is the Dymax® 1187-M UV medical device adhesive. It will be appreciated that any biocompatible adhesive is suitable for use with, in and/or as the backing layer. This layer may also be a nonwoven or porous film double coated with pressure sensitive adhesive. Liquid backing formulations may be moved into the cavities by the same or similar methods as for the active agent casting solution. Where a liquid backing layer formulation is used, the solvent of the backing layer formulation is removed by a drying process. The drying conditions for drying the backing layer should be controlled so that the backing layer solvent can be removed effectively without affecting the stability of an active agent and/or to properly form (e.g. uniform) the backing layer. In one embodiment, the mold is placed into a compressed dry air (CDA) box under controlled air flow and then placed in an oven at about 5-50° C. In further embodiments, the mold is placed in the oven at a temperature of about 5-50° C. In embodiments, the temperature of the CDA and/or oven is about 5° C., about 10° C., about 20° C., about 30° C., about 40° C., about 45° C., or about 50° C. In embodiments, the temperature of the CDA and/or oven is about 5-45° C., 5-40° C., 5-30° C., 5-20° C., 5-15° C., 5-10° C., 10-50° C., 10-45° C., 10-40° C., 10-30° C., 10-20° C., 10-15° C., 15-50° C., 15-45° C., 15-40° C., 15-30° C., 15-20° C., 20-50° C., 20-45° C., 20-40° C., 20-30° C., 30-50° C., 30-45° C., 30-40° C., 30-45° C., 40-50° C., 40-45° C., or 45-50° C. In embodiments, the oven uses convection, conduction, or radiation for drying. In another embodiment, the mold is placed in an oven at about 5-50° C. without prior time in a CDA box. In embodiments, the mold is placed in the CDA and/or oven for at least about 0-120 minutes, about 30-120 minutes, about 30-90 minutes, about 30-60 minutes, about 30-45 minutes, about 45-120 minutes, about 45-90 minutes, about 45-60 minutes, about 60-120 minutes, about 60-90 minutes, about 90-120 minutes, or longer. Residual solvents in the backing layer can be measured to determine the effectiveness of solvent removal under different drying conditions. The backing layer connects and/or supports the microstructure tips.

Figure 4:
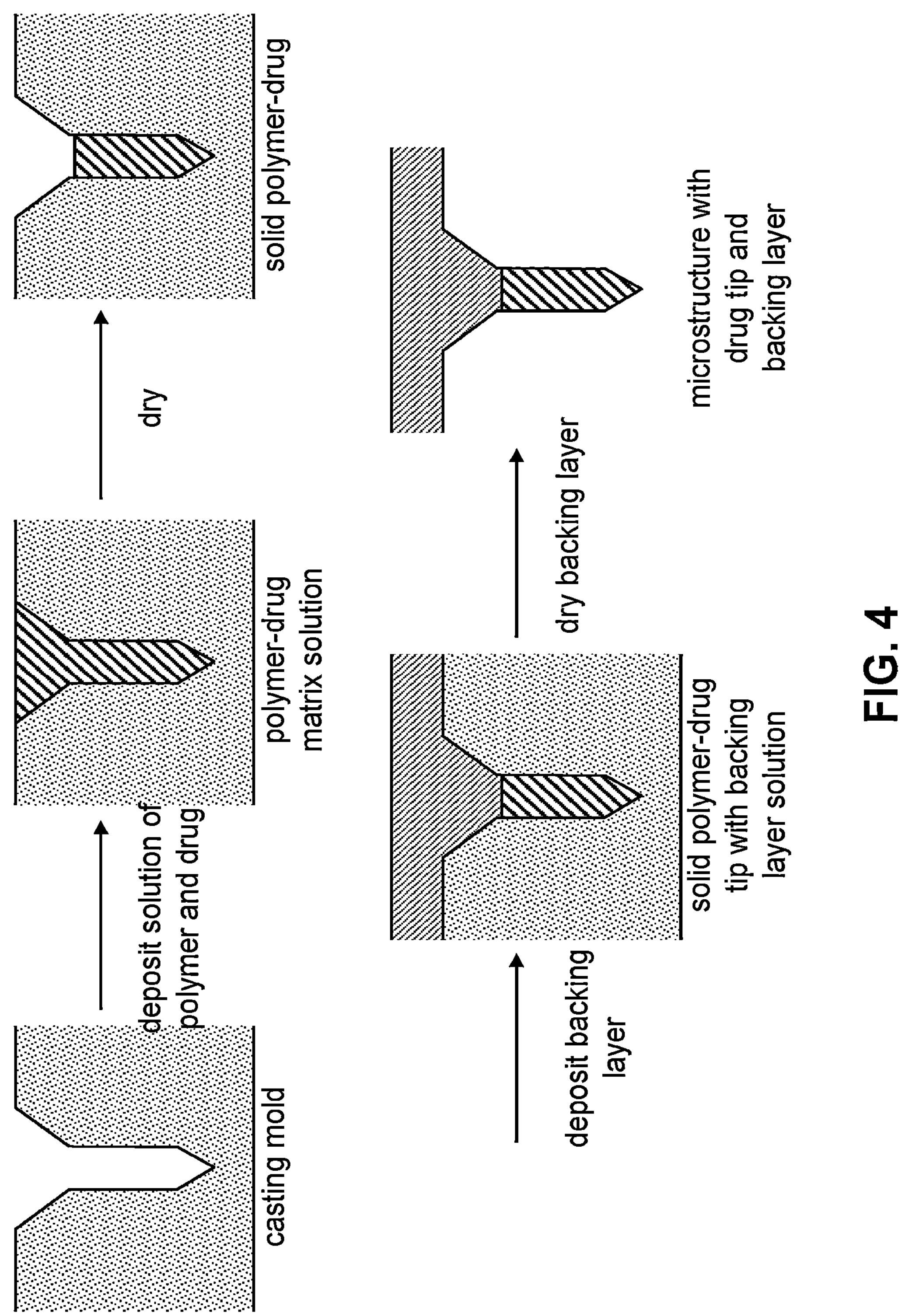
FIG. 4 is an illustration of a method of forming a microstructure array using molds described herein, according to one embodiment.

FIG. 4 is an illustration of a method of forming microstructures having a drug-in-tip (DIT) and a backing layer. A negative casting mold is created from the master mold described in Section I. A liquid DIT casting solution is deposited into the negative casting mold, which of course has at least one cavity in the shape desired for the microstructures. The liquid DIT solution is dried under controlled conditions to remove the solvent, thus creating a solid DIT layer in the bottom or distal end of the cavity. A backing layer is cast on the mold, over the solid DIT layer, such that the remaining space in the cavity is filled and, optionally, a layer of backing layer formulation extends between adjacent cavities. The backing layer is dried such that the resulting array has a backing layer with a plurality of microstructures extending at an angle from the backing layer. The backing layer with attached microstructures is demolded and undergoes a final drying step to form the microstructure array (MSA). It will be appreciated that the MSA may be demolded prior to undergoing the final drying step.

The microstructures may be positioned on a base or substrate to form the array. The substrate may be in addition to or used with a backing layer. The microstructures may be attached to the substrate by any suitable means. In one, non-limiting embodiment, the microstructures are attached to the substrate using an adhesive. Suitable adhesives include, but are not limited to, acrylic adhesives, acrylate adhesives, pressure sensitive adhesives, double-sided adhesive tape, double sided adhesive coated nonwoven or porous film, and UV curable adhesives. One exemplary double-sided tape is the #1513 double-coated medical tape available from 3M. One exemplary, but non-limiting, UV curable adhesive is the 1187-M UV light-curable adhesive available from Dymax. It will be appreciated that any medical device adhesive known in the art would be suitable. In one embodiment, the substrate is a breathable nonwoven pressure sensitive adhesive. The substrate is placed on the backing layer where present or a proximal surface of the microstructures. The substrate is adhered or attached to the microstructures. In another embodiment, the substrate is a UV cured adhesive in a polycarbonate film. The UV adhesive is dispensed on the top of the backing layer or the proximal surface of the microstructures, covered with a polycarbonate (PC) film to spread the adhesive and cured using a UV Fusion system. In one embodiment a UV curing dose is about 1.6 J/cm$^2$. After the substrate is attached or adhered to the microstructures, the microstructure array is removed from the mold. It will be appreciated where the array includes a backing layer the substrate is attached or adhered to the backing layer as described above for the microstructures.

Cast microstructure arrays are removed from the mold by any suitable means. In one embodiment, the microstructure array is removed from the mold by using a de-mold tool. A double-sided adhesive is placed on the back of microstructure array with one side for adhering to the array and the other side for adhering to the de-mold tool. The array is removed from the mold by gently rolling the de-mold tool over the adhesive on the back of the array. The microstructure array is then gently peeled off from the de-mold tool. The arrays may be demolded after drying the backing layer or after a final drying step.

Before or after the microstructure array is removed from the mold a final drying step may be performed under vacuum. The final drying may be at room temperature or at an elevated temperature. In embodiments, the final drying is at about 5-50° C. In embodiments, the final drying is at about 5° C., at about 10° C., at about 20° C., at about 25° C., at about 35° C., at about 40° C., at about 45° C., or at about 50° C. Further suitable temperatures and ranges are described above with reference to drying the backing layer. In embodiments, the final drying is from about 1-24 hours or longer, from about 4-20 hours, from about 6-10 hours, from about 8-16 hours, from about 8-12 hours, from about 8-10 hours, from about 10-12 hours, from about 10-16 hours, from about 12-16 hours or longer. In other embodiments, the final drying step is overnight.

After the microstructure array is removed from the mold, it may be cut to an appropriate size and/or shape. In one embodiment, the microstructure array is die cut with an 11 or 16 mm punch.

Figure 5:
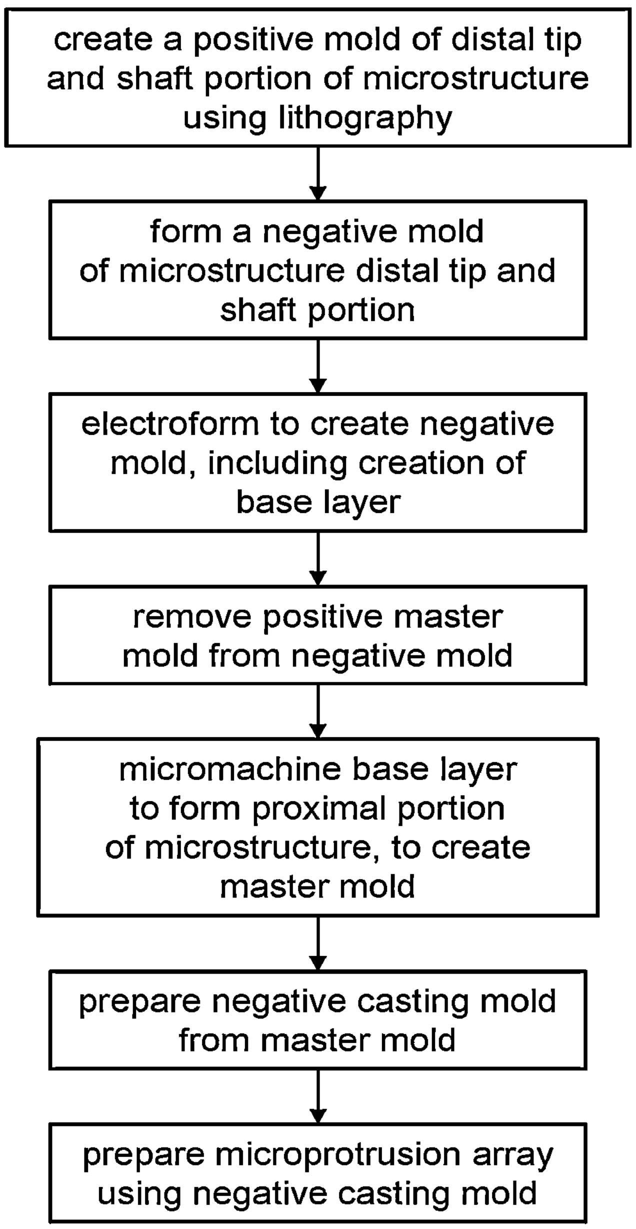
FIG. 5 is a flow chart of a method for preparing a microarray mold and microprotrusion array from the mold, according to one embodiment.

FIG. 5 depicts an overall process that outlines steps for preparing a master mold of a durable material and using the master mold to form a negative casting mold that is used to prepare a microstructure array.

III. Microstructure Arrays

General features of microstructure arrays suitable for use in the instant arrays and methods are described in detail in U.S. Patent Publication No. 2008/0269685, U.S. Patent Publication No. 2011/0006458, and U.S. Patent Publication No. 2011/0276028, the entire contents of which are explicitly incorporated herein by reference.

The microstructure arrays are preferably stable both during the fabrication process as described above and have a stable shelf life. Short-term stability of the arrays may be evaluated by storing the arrays at various temperatures and/or humidities and analyzing monomer content, composition purity, and deamidation of proteins by SEC-HPLC, RP-HPLC, and IEX-HPLC, respectively at specific time points. The liquid casting solution or formulation is preferably stable during the fabrication process, which typically lasts a few hours. Preferably, the liquid casting solution is stable for a period of 30 minutes to 6 hours. In non-limiting embodiments, the liquid casting solution is stable for a period of at least from 30 minutes to 1 hour, from 30 minutes to 2 hours, from 30 minutes to 3 hours, from 30 minutes to 4 hours, from 30 minutes to 5 hours, from 1-6 hours, from 1-5 hours, from 1-4 hours, from 1-3 hours, from 1-2 hours, from 2-6 hours, from 2-5 hours, from 2-4 hours, from 2-3 hours, from 3-6 hours, from 3-5 hours, from 3-4 hours, from 4-6 hours, from 4-5 hours, or from 5-6 hours. In specific, but not limiting embodiments, the liquid casting solution is stable for at least about 30 minutes, about 45 minutes, about 1 hour, about 2 hours, about 3 hours, about 4 hours, about 5 hours, about 6 hours, or longer. The microstructure arrays are preferably stable for at least about one day when stored at about room temperature (e.g. about 25° C.). In other embodiments, the arrays are shelf stable for at least a period of time after fabrication. In some embodiments, the arrays are preferably stable for at least about 1-12 weeks, about 1-16 weeks, or about 1-32 weeks when stored at about 5° C. In other embodiments, the arrays are stable when stored at an elevated temperature (e.g. about 40° C.) for at least about 1-12 weeks, about 1-16 weeks, or about 1-32 weeks. In other embodiments, the arrays are stable when stored at about 5° C. for at least about 1-52 weeks or 1-156 weeks. It will be appreciated that the shelf-life may vary depending on the storage temperature. In embodiments, the arrays are stable when stored at about 5° C. for at least about 1-156 weeks, about 1-12 weeks, about 1-2 weeks, about 1-3 weeks, about 1-4 weeks, about 1-5 weeks, about 2-6 weeks, about 2-5 weeks, about 2-4 weeks, about 2-3 weeks, about 3-6 weeks, about 3-5 weeks, about 3-4 weeks, about 4-6 weeks, about 4-5 weeks, or about 5-6 weeks. In embodiments, the arrays are stable when stored at about 40° C. for at least about 1-26 weeks, about 1-12 weeks, about 1-2 weeks, about 1-3 weeks, about 1-4 weeks, about 1-5 weeks, about 2-6 weeks, about 2-5 weeks, about 2-4 weeks, about 2-3 weeks, about 3-6 weeks, about 3-5 weeks, about 3-4 weeks, about 4-6 weeks, about 4-5 weeks, or about 5-6 weeks. In other embodiments, the arrays are stable when stored at about 25° C. for at least about 1-14 days. In further embodiments, the arrays are stable when stored at about 25° C. for at least about 1-12 weeks, about 1-16 weeks, about 1-104 weeks, or about 1-156 weeks. In specific, but not limiting, embodiments, the arrays are stable when stored at about 5° C. for at least about 5 days, at least about 1 week, at least about 2 weeks, at least about 4 weeks, at least about 5 weeks, at least about 6 weeks, or longer. In embodiments, the arrays are stable when stored at about 25° C. for at least about 1-2 days, about 1-5 days, about 1-7 days, about 1-10 days, about 2-5 days, about 2-7 days, about 2-10 days, about 2-14 days, about 3-5 days, about 3-7 days, about 3-10 days, about 3-14 days, about 5-14 days, about 5-10 days, about 5-14 days, or about 10-14 days. In specific, but not limiting, embodiments, the arrays are stable when stored at about 25° C. for at least about 12 hours, at least about 1 day, at least about 2 days, at least about 3 days, at least about 4 days, at least about 5 days, at least about 6 days, at least about one week, or longer. Stability is typically monitored by measuring the purity of the active agent in the array after storage as compared to an array before storage (time=0). In embodiments, the array has a purity of at least about 80-100%, about 85-100%, about 90-100%, about 95-100%, about 80-95%, about 85-95%, about 90-95% about 80-90%, about 85-90% or about 80-85% after storage. In non-limiting embodiments, the array has a purity of at least about 80%, about 85%, about 90%, about 92%, about 93%, about 95%, about 96%, about 97%, about 98%, about 99%, or about 100% after storage.

Where the active agent is a protein, Methionine-oxidation (Met-oxidation) is preferably less than or equal to 1-20% after storage for about 1-6 weeks at about 5° C.-40° C. In embodiments Met-oxidation is less than about 1-10%, about 1-5%, about 1-6%, about 2-3%, about 2-4%, about 2-5%, 2-6%, about 3-5%, or about 3-6%. In specific, but not limiting, embodiments, Met-oxidation is less than about 1%, about 2%, about 3%, about 4%, about 5%, about 6%, or about 10%.

The microstructure arrays should have sufficient mechanical strength to at least partially penetrate the stratum corneum or other membrane surface of a subject. It will be appreciated that different mechanical strength will be required for application at different sites. One method for assessing mechanical strength is a skin-penetration efficiency (SPE) study as described in Example 7. Preferably, the arrays have a SPE of about 50-100%. In other embodiments, the arrays have a SPE of about 50-80%, about 50-85%, about 50-90%, about 50-95%, about 60-80%, about 60-85%, about 60-90%, about 60-95%, about 60-100%, about 75-80%, about 75-85%, about 75-90%, about 75-95%, about 75-100%, about 80-85%, about 80-90%, about 80-95%, about 80-100%, about 90-95%, and about 90-100%. In specific, non-limiting, embodiments, the arrays have a SPE of about 50%, 60%, 70%, 75%, 80%, 85%, 90%, 95%, 99%, and 100%.

Preferably, at least about 50-100% of the active agent is delivered by the MSAs described herein. Delivery efficiency may be determined by preparing the MSA and applying the MSA in vivo or in vitro as described in Example 7. In embodiments, the MSA has a delivery efficiency of at least about 50-60%, about 50-70%, about 50-75%, about 50-80%, about 50-90%, about 50-95%, about 50-99%, about 60-70%, about 60-75%, about 60-80%, about 60-90%, about 60-95%, about 60-99%, about 70-75%, about 70-80%, about 70-90%, about 70-95%, about 70-99%, about 75-80%, about 75-90%, about 75-95%, about 75-99%, about 80-90%, about 80-95%, about 80-99%, about 90-95%, about 90-99%, or about 95-99%.

IV. Methods of Use

The methods, kits, microstructure arrays and related devices described herein may be used for treating any condition. It will be appreciated that the microstructure arrays may be used with any appropriate applicator including the applicator described in U.S. Publication No. 2011/0276027, as well as those described in U.S. Publication No. 2014/0276580 and 2014/0276366, each of which are incorporated herein in their entirety.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

All patents, patent applications, and publications mentioned herein are hereby incorporated by reference in their entireties. However, where a patent, patent application, or publication containing express definitions is incorporated by reference, those express definitions should be understood to apply to the incorporated patent, patent application, or publication in which they are found, and not necessarily to the text of this application, in particular the claims of this application, in which instance, the definitions provided herein are meant to supersede.

What is claimed is:

1. A method of forming a master mold, comprising:

a) forming a plurality of microstructure portions in a substrate formed of a first material by a first micromachining process, each microstructure portion comprising a shaft and a distal tip;

b) preparing a negative mold of the plurality of microstructure portions, wherein the mold is formed of a second material and comprises a plurality of cavities corresponding to each microstructure portion in the plurality of microstructure portions;

c) electroplating a metal onto the negative mold to fill each cavity in the plurality of cavities and to form a base layer extending from the negative mold;

d) forming a proximal section for each of the microstructures in the base layer using a second micromachining process; and e) before or after said step d), removing the negative mold from the metal to form a master mold.

2. The method of claim 1, wherein the second micromachining process is a mechanical micromachining process.

3. The method of claim 1, wherein the first material is selected from silicon and a positive photoresist material.

4. The method of claim 1, wherein said first micromachining process comprises a photolithography process.

5. The method of claim 4, wherein said photolithography comprises:

1) Applying a layer of photoresist on the first material;

2) Applying a masking material onto the photoresist layer, wherein the masking material covers at least a portion of the photoresist layer;

3) Curing the portion of the photoresist layer not covered by the masking material;

4) Isotropic etching the substrate to create the distal tip section;

5) Etching the substrate to create the shaft portion;

6) Wet thermal oxidizing the microstructures; and

7) Isotropic wet etching the microstructures.

6. The method of claim 5, wherein the first material is silicon, and the method further comprises forming a layer of silicon dioxide on the silicon substrate using a thermal oxidation process prior to step 1.

7. The method of claim 5, wherein the thermal oxidation process in step 1 is a wet thermal oxidation process.

8. The method of claim 5, wherein the photoresist material is an epoxy-based negative photoresist.

9. The method of claim 8, wherein the photoresist material is SU-8.

10. The method of claim 5, wherein the masking material comprises a plurality of apertures, wherein the photoresist layer exposed by the apertures is cured in step 3.

11. The method of claim 5, further comprising:

removing the masking material and any uncured photoresist material after step 3.

12. The method of claim 11, wherein the masking material and uncured photoresist are removed using a solvent.

13. The method of claim 5, wherein the etching of step 5 comprises anisotropic etching.

14. The method of claim 5, wherein step 5 comprises deep reactive-ion etching.

15. The method of claim 5, further comprising:

prior to step 1, cleaning a polymeric material.

16. The method of claim 15, wherein said cleaning comprises chemical cleaning.

17. The method of claim 16, wherein the chemical cleaning comprises an RCA cleaning process.

18. The method of claim 5, wherein step 4 and/or step 5 comprises plasma etching.

19. The method of claim 18, wherein the plasma etching comprises a plasma gas selected from SF6, carbon tetrachloride, oxygen, and $CHF_3$.

20. The method of claim 5, further comprising removing any remaining photoresist from the first material after step 5.

21. The method of claim 1, wherein the second material is one of a polymeric material and a silicon material.

22. The method of claim 21, wherein the second material is selected from the group consisting of polydimethylsiloxane (PDMS), polycarbonate, polyetherimide, and polyethylene terephthalate.

23. The method of claim 1, wherein the electroplating metal is selected from copper, nickel, chromium, and gold.

24. The method of claim 1, wherein the proximal section is micromachined to have a funnel or pyramidal shape.

25. A method of forming a casting mold comprising:

preparing a negative mold of the master mold formed in claim 1.

26. A method of preparing a microstructure array, comprising:

dispensing a polymer matrix solution or suspension comprising at least one therapeutic agent on a casting mold of claim 25;

drying the polymer matrix solution;

dispensing a polymer matrix backing solution on the casting mold;

drying the polymer matrix backing solution to form the microstructure array; and demolding the microstructure array.

* * * * *